United States Patent [19]

Walser et al.

[11] 4,166,185
[45] Aug. 28, 1979

[54] IMIDAZO[1,5-a][1,4]BENZODIAZEPINES

[75] Inventors: Armin Walser, West Caldwell; Rodney I. Fryer, North Caldwell; Louis Benjamin, Livingston, all of N.J.

[73] Assignee: Hoffmann-La Roche Inc., Nutley, N.J.

[21] Appl. No.: 928,628

[22] Filed: Jul. 27, 1978

Related U.S. Application Data

[62] Division of Ser. No. 776,820, Mar. 11, 1977.

[51] Int. Cl.² .......................................... C07D 487/04
[52] U.S. Cl. ............................ 548/324; 260/239 BD; 548/302; 424/273 R
[58] Field of Search ........................................ 548/324

[56] References Cited

U.S. PATENT DOCUMENTS 3,763,179  10/1973  Gall ...................................... 548/324
3,852,461  12/1974  Hester, Jr. et al. .................. 548/324

Primary Examiner—Natalie Trousof
Assistant Examiner—Robert C. Whittenbaugh
Attorney, Agent, or Firm—Jon S. Saxe; Bernard S. Leon; Frank P. Hoffman

[57] ABSTRACT

Compounds are disclosed of the formula

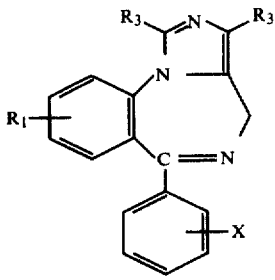

and

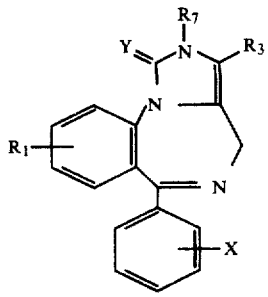

wherein $R_1$ is hydrogen, halogen or trifluoromethyl; $R_2$ is selected from the group consisting of lower alkylthio together with the sulfoxide and sulfone thereof, halo, lower alkylamino or lower alkoxy; Y is oxo or thio; $R_3$ is selected from the group consisting of hydrogen, —COOR$_4$ wherein $R_4$ is hydrogen or lower alkyl, —CONR$_6$R$_5$ wherein $R_5$ and $R_6$ are hydrogen or lower alkyl; X is hydrogen or halogen; and $R_7$ is lower alkyl or hydrogen and the pharmaceutically acceptable salts and N-oxides thereof.

Also presented are processes to produce the above compounds and intermediates therefor and derivatives thereof.

1 Claim, No Drawings

IMIDAZO[1,5-a][1,4]BENZODIAZEPINES

This is a division of application Ser. No. 776,820 filed Mar. 11, 1977.

DESCRIPTION OF THE INVENTION

The present invention relates to compounds of the formula

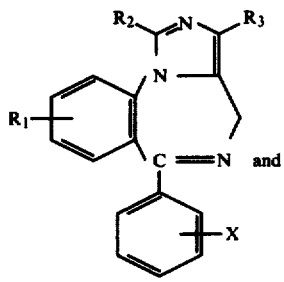

and

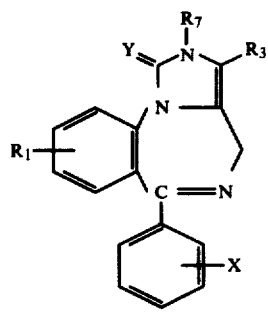

wherein $R_1$ is hydrogen, halogen or trifluoromethyl; $R_2$ is selected from the group consisting of lower alkylthio together with the sulfoxide and sulfone thereof, halo, lower alkylamino or lower alkoxy; Y is oxo or thio; $R_3$ is selected from the group consisting of hydrogen, —$COOR_4$ wherein $R_4$ is hydrogen or lower alkyl; —$CONR_6R_5$ wherein $R_5$ and $R_6$ are hydrogen or lower alkyl; X is hydrogen or halogen; and $R_7$ is lower alkyl or hydrogen and the pharmaceutically acceptable salts and N-oxides thereof.

As used in this disclosure, the term "lower alkyl" or "alkyl" comprehends both straight and branched chain ($C_1$ to $C_7$) carbon-hydrogen radicals, preferably $C_1$ to $C_4$ carbon-hydrogen radicals such as methyl, ethyl, propyl, isopropyl, butyl and the like.

The term "halogen" is used to include all four forms thereof, i.e., chlorine, bromine, fluorine and iodine.

The compounds of the present invention exhibit pharmacological activity as sedatives, muscle relaxants, anxiolytics and anticonvulsants.

The following reaction scheme sets forth the processes utilized to produce the novel compounds of the present invention.

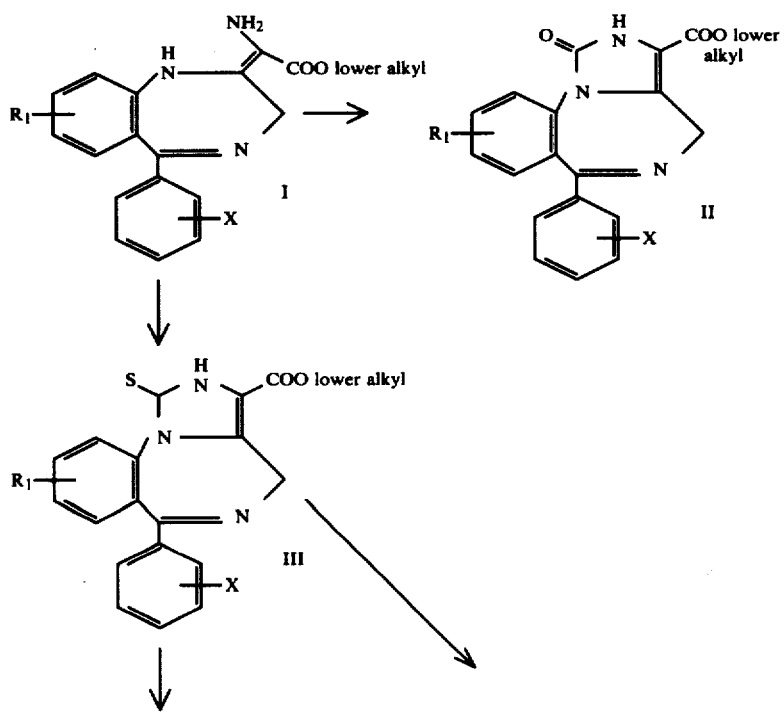

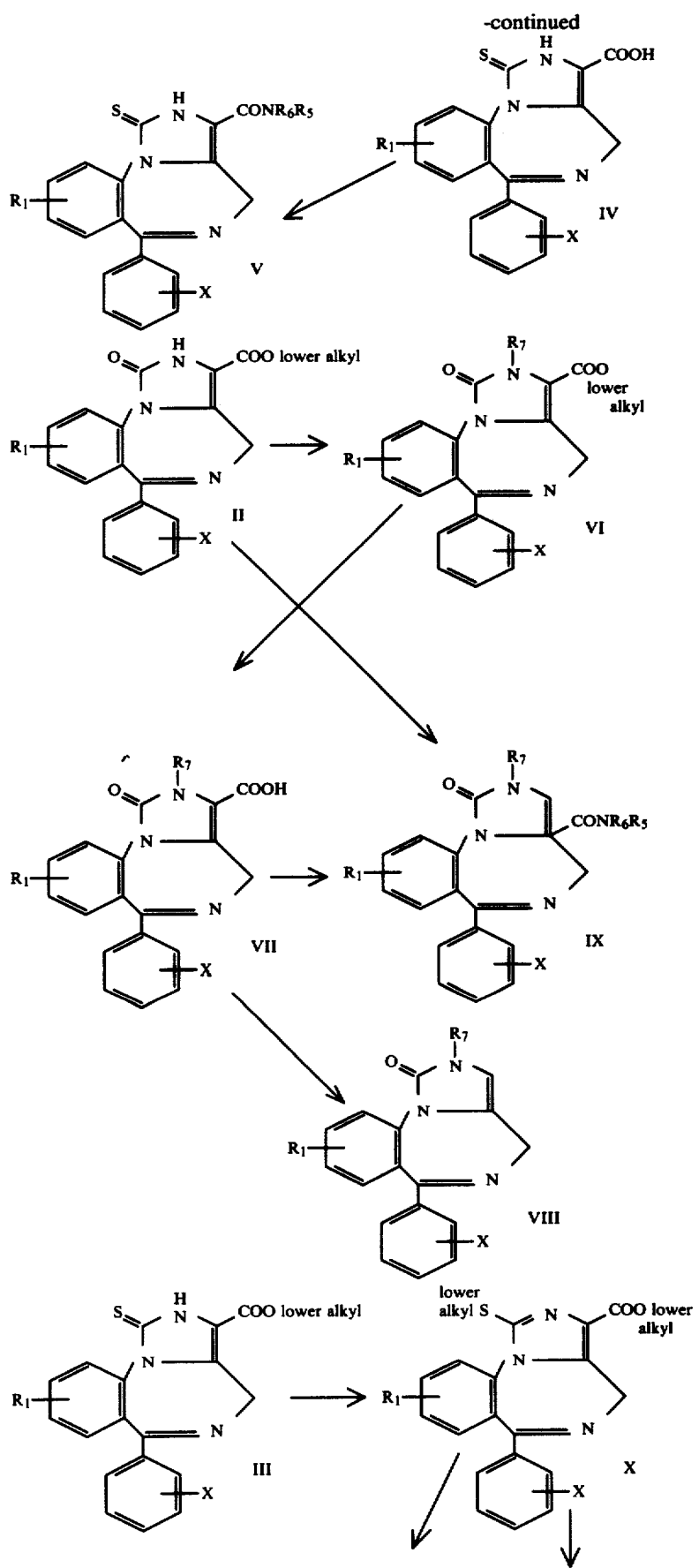

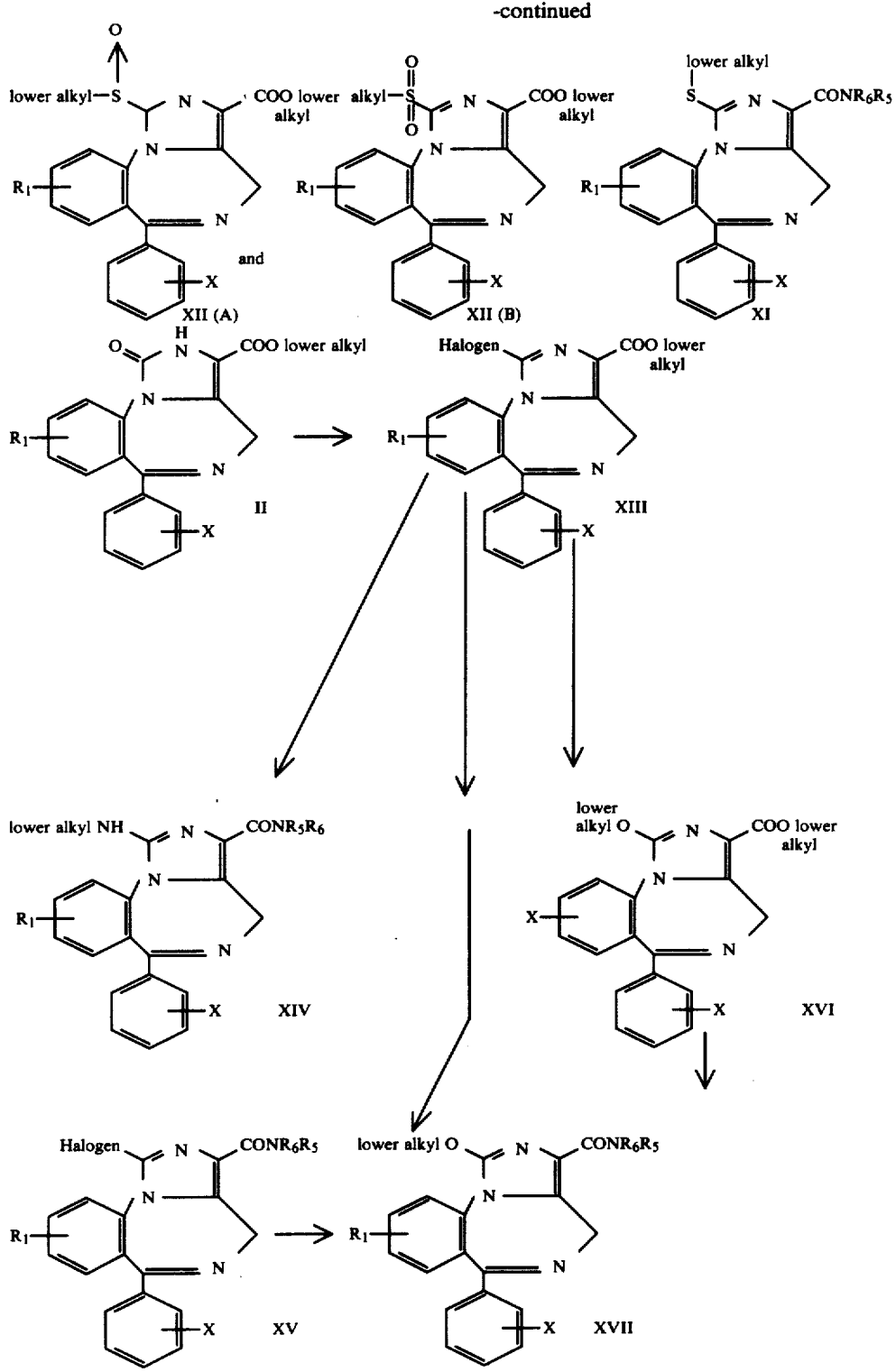

I→II

Compounds of the formula I are known in the prior art. Methods for their preparation are disclosed, for instance, in Belgian Pat. No. 833,248 of Mar. 10, 1976. The compound of formula I is reacted with phosgene in the presence of an acid acceptor, such as an organic or inorganic base, e.g., pyridine, triethylamine, potassium carbonate or, preferably, a hydrogen chloride scavenger, such as 1,2-epoxy-3-phenoxypropane. The reaction is effected at a temperature of between −50° C. to room temperature with 0° C. preferred. Solvents suitable for the reaction include aliphatic or aromatic hydrocarbons or chlorinated hydrocarbons, e.g., benzene, toluene, xylene, chlorobenzene or preferably methylene chloride ethers, e.g., THF.

I→III

Reaction of a compound of formula I with thiophosgene results in the thiocompound of formula III. The reaction parameters are as in Step I II.

II→VI

The compound of formula II is alkylated by initial reaction with a strong base such as sodium methoxide, potassium-t-butoxide, sodium hydride, etc. Thereafter a subsequent reaction with lower alkyl halide, e.g., methyl iodide or a dialkyl sulfate, e.g., dimethyl sulfate is carried out in situ. Solvents suitable for such a reaction include lower alkanols ($C_1$-$C_4$), ethers, DMF and DMSO. The reaction temperature may be varied from −30° C. to 50° C. with room temperature preferred.

II, III or VI→IV or VII, respectively

The esters of formulas II or III may be hydrolyzed to the corresponding acids by reaction with an alkali metal hydroxide such as sodium or potassium hydroxide in solvents such as $C_1$ to $C_4$ alcohols, ethers, DMSO or water or aqueous mixtures thereof. The reaction temperature is in the range of room temperature to reflux temperature with reflux temperature of the selected solvent as preferred.

II or III→IX or V, respectively

The esters of formulas II or III may be converted directly to the primary or secondary amides by reaction with ammonia or a lower alkylamine in an autoclave or sealed vessel under high pressure, i.e., above atmospheric pressure. Solvents for such a reaction include $C_1$-$C_4$ alcohols, pyridine, DMSO, ethers or the alkylamines may be utilized as solvents themselves. The temperature of the reaction may be varied from 100° C. to 150° C. with 130° C. as preferred.

VII or IV→IX or V, respectively

The acids of formulas VII or IV may also be converted to the corresponding primary, secondary or tertiary amides by reaction of the particular acid with an agent such as thionyl chloride or phosphorus pentachloride to form the acid chloride and thereafter converting the acid chloride to the amide by reaction with ammonia or lower alkylamine. Solvents for such a reaction include chlorinated hydrocarbons, such as chloroform or methylene chloride or aromatic hydrocarbons, such as benzene or toluene. The reaction temperature may vary from −20° C. to 50° C. with room temperature as preferred.

III→X

The ester of formula III is converted to the corresponding alkylthio compound by reaction with an alkyl or dialkyl sulfate in the presence of a strong base such as sodium methoxide, potassium-t-butoxide or sodium hydride. Solvents suitable for such a reaction include $C_1$-$C_4$ alcohols, ethers, DMF and DMSO. The reaction may vary between −30° C. to reflux temperature of the selected solvent with room temperature preferred.

X→XI

The ester of formula X may be converted to the acid intermediate and thereafter converted to the primary, secondary or tertiary amide or X may be directly converted to the primary and secondary amide. The reaction parameters (agent, solvents, temperature, etc.) are the same as those for Steps II or III→VII or IV; II or III→IX or V' and VII or IV→IX or V above.

VII→VIII

The acid of formula VII may be decarboxylated to the compound of formula VIII by pyrolysis, i.e., heating to between 160° C. to 250° C. with or without solvent present. Solvents which may be utilized include trichlorobenzene, ethylene glycol or mineral oil.

X→XII(A) and XII(B)

The alkylthio compound of formula X may be oxidized to the sulfoxide and sulfone compounds XII(A and B) by treatment with hydrogen peroxide or organic peracids such as meta-chloroperbenzoic acid. Solvents for such a reaction include methylene chloride, chloroform or acetic acid. The temperature range for the reaction ranges from −20° C. to room temperature with 0° C. as most preferred although the variation of temperature will determine the relative percentage of sulfoxide versus sulfone as end product along with the amount of oxidizing agent utilized. The sulfone and sulfoxide compounds may be separated by fractional crystallization or by chromatographic methods known in the art.

II→XIII

Conversion of the oxo compound of formula II to the halogenated compound is effected by reaction with phosphorus-oxyhalides, e.g., phosphorus-oxybromide or phosphorus-oxychloride or phosphorus-pentachloride. Solvents for the reaction include hydrocarbons, e.g., benzene or toluene, chlorinated hydrocarbons, e.g., methylene chloride or chlorobenzene or the reagents themselves can function as solvents. The temperature range of the reaction can vary from about 60° C. to reflux temperature of the selected solvent with reflux temperature as preferred.

XIII→XV

The reaction of the ester compound of formula XIII to the primary, secondary or tertiary amide is effected by utilizing the reaction parameters (reagents, solvents, temperatures, etc.) as in Steps II or III→VII or IV; II or III→IX or V; and VII or IV→IX or V above, i.e., directly or through the acid.

XIII→XVI

The halogen of the compound of formula XIII may be displaced with an alkali metal alkoxide, e.g., sodium methoxide or potassium ethoxide. The solvent chosen for the reaction should represent the corresponding alcohol ($C_1$-$C_7$) preferably ($C_1$-$C_4$) or mixtures of inert solvents such as ethers, DMF and DMSO. The reaction temperature ranges from about 60° C. to about 150° C. with about 120° C. as preferred.

XVI→XVII

The conversion of the ester of formula XVI to the amide follows the reaction parameters set forth in Steps II or III→VII or IV; II or III→IX or V; and VII or IV→IX or V above, i.e., through the acid or directly from the ester.

XIII→XIV

The reaction of the ester compound of formula XIII to the primary or secondary amide is effected by utilizing the reaction parameters as in Step XIII→XV except that the reaction conditions are more rigorous, i.e, at a higher temperature and longer reaction time, e.g., at or above 120° C. with the reaction time prolonged, e.g., over 2 days.

It should be noted that where the ortho substituent on the phenyl moiety is fluorine, the vigorous direct amination step (ester to amide) of steps XIII→XIV or XVI would most probably also be accompanied by displacement of the fluorine by the amine or alkoxide.

XV→XVII

Compounds of the formula XV may thereafter be converted to compounds of the formula XVII by reaction with an alkali metal alkoxide, e.g., sodium methoxide or potassium ethoxide. The reaction parameters are as in Step XIII→XVI.

An additional reaction scheme to produce compounds of the present invention is as follows:

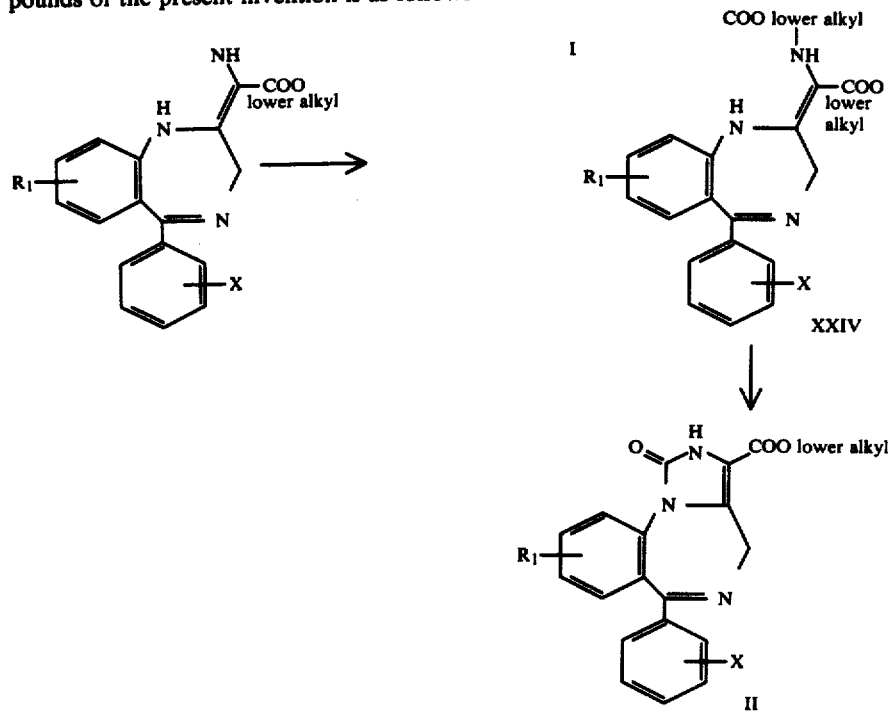

I→XXIV

The compound of formula I may be reacted with lower alkyl haloformates, such as, ethylchloroformate, which may be generated in situ by reaction of phosgene and ethanol to give the compounds of formula XXIV. Other reaction parameters are as in Step I→II.

XXIV→II

The compound of formula XXIV is thereafter cyclized by treatment with strong base such as sodium methoxide, potassium-t-butoxide, sodium hydride, etc. Solvents for the reaction include DMF, THF and DMSO. The reaction temperature ranges from about 80° C. to about 150° C. with about 100° C. as preferred.

Yet another reaction scheme to produce the compounds of the present invention is as follows:

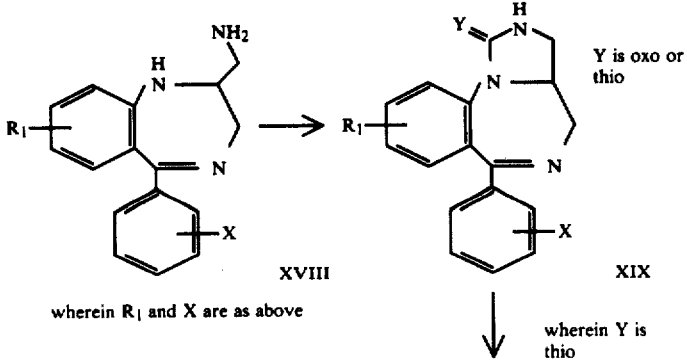

wherein $R_1$ and X are as above

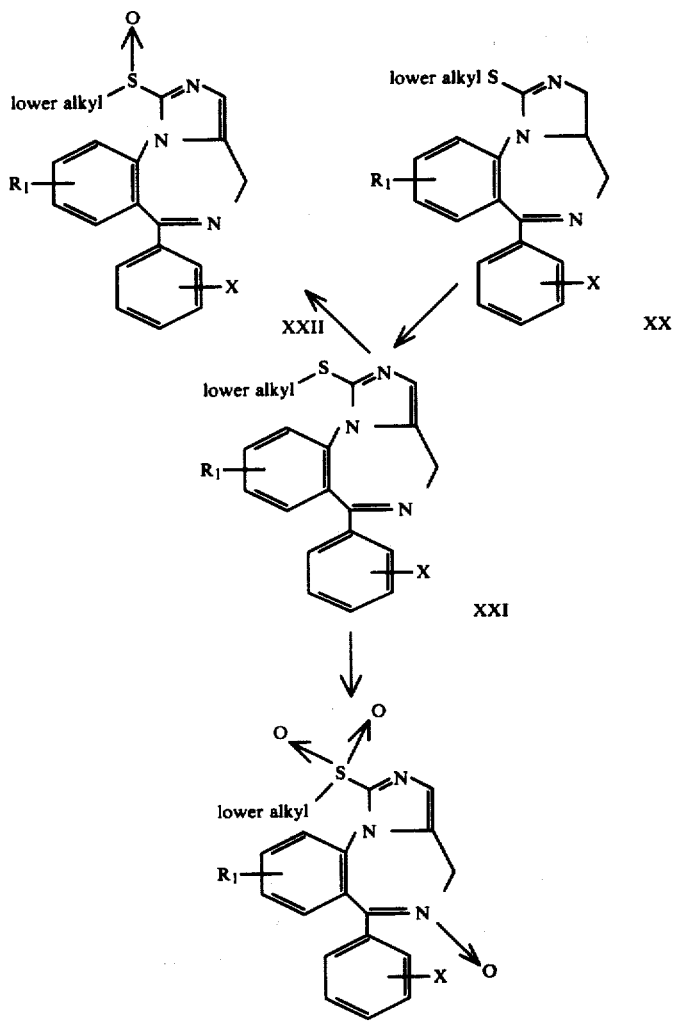

XVIII→XIX

The compound of formula XVIII is known in the art and a method for its preparation has been disclosed in Belgian Pat. No. 833,248 issued Mar. 10, 1976. The compound of formula XVIII may be reacted with phosgene (if the oxo analog is desired) or with thiophosgene to produce the thio-compound of formula XIX. The reaction parameters, i.e., the reagents, solvents, reaction temperatures, etc., are as described in Steps I→II or in this instance I→III.

XIX→XX

The compound of formula XIX is thereafter alkylated by initial reaction with a strong base such as sodium hydroxide, sodium methoxide, sodium hydride, etc. Thereafter, a subsequent reaction with a dialkyl sulfate, e.g., dimethylsulfate or a lower alkyl halide, e.g., methyl iodide is carried out in situ. Solvents for such a reaction include lower ($C_1$-$C_4$) alcohols, ethers, DMF and DMSO. The reaction temperature may be varied from about −30° C. to about 50° C. with room temperature preferred.

XX→XXI

The compound of formula XX is thereafter oxidized to the unsaturated compound by reaction with manganese dioxide in an inert hydrocarbon, e.g., benzene, toluene, etc., or chlorinated hydrocarbons, e.g., chlorobenzene. The temperature of the reaction may vary from about 80° C. to 150° C. with reflux temperature of the solvent being preferred.

XXI→XXII or XXIII

The compound of formula XXI may therafter be oxidized to the sulfoxide (XXII) or the sulfone-N-oxide (XXIII) by reaction with hydrogen peroxide or an organic peracid, such as perbenzoic acid or peracetic acid. Solvents for such a reaction include acetic acid or chlorinated hydrocarbons, such as chlorobenzene or methylene chloride. The temperature may range from −20° C. to 100° C. with room temperature being preferred for production of the sulfoxide (XXII). The sulfone-N-oxide is produced by utilizing an excess of reagent, i.e., hydrogen peroxide or peracid and by using increased temperature, i.e., 50° C. to 100° C., with 100° C. being preferred. Increase of reaction time will also bring about the predominance of the N-oxide (XXIII).

The compounds of the present invention exhibit pharmacological activity as anxiolytics, sedatives, muscle relaxants and anticonvulsants. As contemplated by this invention, the novel compounds of the present invention and their pharmaceutically acceptable salts can be embodied in pharmaceutical dosage formulations containing from about 0.1 to about 200 mg., most preferably 1-100 mg., with the dosage adjusted to species and individual patient requirements. The novel compounds and their pharmaceutically acceptable salts can be administered internally, for example, parenterally or enterally, in conventional pharmaceutical dosage forms. For example, they can be incorporated in conventional liquid or solid vehicles such as water, gelatin, starch, magnesium stearate, talc, vegetable oils and the like to provide tablets, elixirs, capsules, solutions, emulsions and the like according to acceptable pharmaceutical practices.

The expression "pharmaceutically acceptable salts" is used to include both inorganic and organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluenesulfonic acid and the like. Such salts can be formed quite readily by those skilled in the art, with the prior art and the nature of the compound to be placed in salt form, in view.

A preferred genus are compounds of the formula

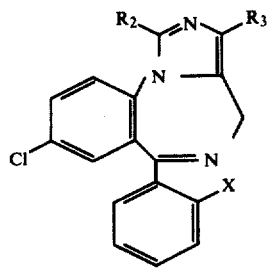

wherein X is hydrogen, chloro or fluoro; $R_2$ is —O—alkyl, chloro, —S—alkyl or $NHCH_3$; $R_3$ is $CONH_2$,

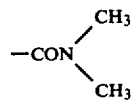

or —$COOCH_3$.

EXAMPLE 1

[7-Chloro-1,3-dihydro-5-(2-fluorophenyl)-2H-1,4-benzodiazepin-2-ylidene]-alpha-(ethoxycarbonylamino)acetic acid, methyl ester A solution of 7.5 g (0.02 mole) of 7-chloro-5-(2-fluorophenyl)-α-hydroxyimino-3H-1,4-benzodiazepine-2-acetic acid, methyl ester in 150 ml of dimethylformamide and 50 ml of ethanol was hydrogenated over Raney nickel (1 teaspoonful) at atmospheric pressure for 2½ hours. The catalyst was filtered and 10 ml of pyridine was added to the filtrate. After cooling to −20°, 30 ml of a 10% solution of phosgene in benzene was added with stirring. The reaction mixture was allowed to reach room temperature and was then evaporated under reduced pressure to dryness. The residue was partitioned between methylene chloride and saturated sodium bicarbonate solution. The organic phase was dried and evaporated. The residue was chromatographed over 300 g of silica gel using 20% (v/v) of ethyl acetate in methylene chloride. Crystallization of the combined clean fractions from ether yielded yellowish crystals. The analytical sample was recrystallized from methylene chloride/ethyl acetate/hexane and gave off-white crystals with mp 188°-191°. Uv λ infl. 242 mμ (ε=20800) infl 275 (10500) max 313 (30800) infl ca 365 (3400) ir ($CHCl_3$) 3400 cm$^{-1}$, 3250, 3200 (NH) 1720 (COOEt) 1665 ($COOCH_3$) 1620; nmr ($CDCl_3$) δ 1.25 (t, 3, J=7 Hz, —$CH_2\underline{CH_3}$) 3.72 (s, 3, $OCH_3$) 4.13 (q, 2, J=7 Hz, —$O\underline{CH_2}$—) 4.43 (broad s, 2, —$CH_2$—) 5.83 (s, 1, NH) 6.8–7.8 (m, 7, aromatic H) 11.0 (s, 1, NH).

Anal. Calcd. for $C_{21}H_{19}ClFN_3O_4$: C, 58.41; H, 4.43; N, 9.73. Found: C, 58.32; H, 4.39; N, 9.72.

EXAMPLE 2

8-Chloro-6-(2-chlorophenyl)-1,2-dihydro-1-oxo-4H-imidazo[1,5-a][1,4]benzodiazepine-3-carboxylic acid methyl ester A stirred solution of 15 g (0.04 mole) of 2-[(amino)-methoxycarbonylmethylene]-7-chloro-5-(2-chlorophenyl)-1,3-dihydro-2H-1,4-benzodiazepine and 12 g (0.08 mole) of 1,2-epoxy-3-phenoxypropane in 150 ml of methylene chloride was cooled in an ice-salt bath and treated with 47 g (0.06 mole) of a 12.5% solution of phosgene in benzene at a moderate rate. Stirring in the cold under a drying tube was continued for 2 hours. A cold solution of 3 N ammonium hydroxide (50 ml) was added and stirring was continued for 10 min. The organic phase was separated, dried over sodium sulfate and evaporated under reduced pressure. Stirring the oily residue with anhydrous ether gave off-white crystals. The crystals were filtered, washed with ether and air dried on the funnel to yield the end product. Recrystallization from ethanol methylene chloride gave white needles with mp 273°-276° (dec). Uv λ max 223 mμ (ε=43800) 276 (21100) infl 348 (1100) ir (KBr) 3150 (NH) 1720 (COOMe, CO) nmr ($CDCl_3$) δ 3.80 ppm (s, 3, $OCH_3$) 4.11 (broad d, 1) and 5.58 (broad d, 1) (AB-system, J=12 Hz, $C_4$—H) 6.95 (d, 1, J=2.5 Hz, $C_7$—H) 7.3–7.8 (m, 5, aromatic H) 7.96 (d, 1, J=8 Hz, $C_{10}$—H) 11.19 (broad s, 1, NH).

Anal. Calcd. for $C_{19}H_{13}Cl_2N_3O_3$: C, 56.74; H, 32.6; N, 10.45. Found: C, 56.89; H, 3.43; N, 10.35.

EXAMPLE 3

8-Chloro-1,2-dihydro-6-(2-fluorophenyl)-1-oxo-4H-imidazo[1,5-a][1,4]benzodiazepine-3-carboxylic acid, methyl ester, and 8-chloro-1,2-dihydro-6-(2-fluorophenyl)-1-oxo-6H-imidazo[1,5-a][1,4]benzodiazepine-3-carboxylic acid, methyl ester Potassium t-butoxide, 1.2 g (0.0107 mole), was added to a solution of 4.32 g (0.01 mole) of [7-chloro-1,3-dihydro-5-(2-fluorophenyl)-2H-1,4-benzodiazepin-2-ylidine]-α-(ethoxycarbonylamino) acetic acid methyl ester in 50 ml of dry dimethylformamide. The reaction mixture was stirred under nitrogen and slowly heated up to 115°-120°, then cooled, acidified by addition of 1 ml of glacial acetic acid and partitioned between methylene chloride and saturated sodium bicarbonate solution. The organic phase was washed with water, dried and evaporated. Crystallization of the residue from ethyl acetate yielded a mixture of the two isomeric products which were separated by chromatography over 250 g of silica gel using methylene chloride/ethyl acetate 2:1. The less polar component (6H) was crystallized from methylene chloride/ether to give colorless crystals which were recrystallized from tetrahydrofuran/ethanol for analysis, mp 262°-264°. Uv λ infl 240 mμ (ε-7900) infl 255 (6600) max 261 (7100) 267 (7000) infl 280 (5200) max 331 (13250) ir (KBr) 1720 cm$^{-1}$ (COOCH$_3$); nmr (d-DMSO) δ 3.83 (s, 3, OCH$_3$) 5.95 (d, 1, J=2 Hz, C$_6$—H) 6.5 (s, 1, J=2 Hz, C$_7$—H) 7.0–8.3 (m, 6, aromatic H) 8.55 (d, 1, J=2 Hz, C$_4$—H) 11.9 (broad s, 1, NH).

Anal. Calcd. for C$_{19}$H$_{13}$ClFN$_3$O$_3$: C, 59.16; H, 3.40; N, 10.89. Found: C, 59.12; H, 3.33; N, 10.67.

The more polar major component was crystallized from methylene chloride/ethyl acetate to yield the 4H compound with mp 252°–254°. Uv λ in fl 213 mμ (ε=34000) max 278 (21450) infl 285 (20700); ir (KBr) 1720 cm$^{-1}$, 1705 (COOCH$_3$, CO) nmr (CDCl$_3$) δ 3.8 ppm (s, 3, OCH$_3$) 4.1 (d, 1) and 5.56 (d, 1) (AB-system), J=12.5 Hz, C$_4$—H) 7.7.8 (m, 5, aromatic H) 7.97 (d, 1, J=8 Hz, C$_{10}$—H) 11.25 (broad s, 1, NH).

Anal. Calcd. for C$_{19}$H$_{13}$ClFN$_3$O$_3$: C, 59.15; H, 3.40; N, 10.89. Found: C, 59.22; H, 3.24; N, 11.05.

EXAMPLE 4

8-Chloro-6-(2-chlorophenyl)-1,2-dihydro-4H-imidazo[1,5-a][1,4]benzodiazepin-1-thione-3-carboxylic acid, methyl ester A stirred solution of 15 g (0.04 mole) of 2-[(amino)-methoxycarbonylmethylene]-7-chloro-5-(2-chlorophenyl-1,3-dihydro-2H-1,4-benzodiazepine and of 12 g (0.08 mole) of 1,2-epoxy-3-phenoxypropane in 80 ml of methylene chloride was cooled in an ice-salt bath and treated rapidly with a solution of thiophosgene (7 g, 0.06 mole) in 70 ml of methylene chloride. Stirring in the cold under a drying tube was continued for 2 hours. Cold 3 N ammonium hydroxide solution (50 ml) was added and stirring in the cold was continued for an additional 30 min. The organic layer was washed with 6 N hydrochloric acid, dried over sodium sulfate and evaporated. The oily residue was stirred with ether to give a light tan solid with mp ca. 230°. Recrystallization from ethanol/methylene chloride gave light tan plates with mp 232°–235°. Uv λ0 max 220 mμ (ε=55500) 297 (14300) ir (KBr) 1720 cm$^{-1}$; nmr (d-DMSO) δ 3.84 ppm (s, 3, OCH$_3$) 4.05 (d, 1) and 5.59 (d, 1) (AB-system, J=12 Hz, C$_4$—H) 7.01 (d, 1, J=2.5 Hz, C$_7$—H) 7.3–7.8 (m, 5, aromatic H) 8.39 (d, 1, J=8 Hz, C$_{10}$—H) 13.28 (broad s, 1, NH).

Anal. Calcd. for C$_{19}$H$_{13}$Cl$_2$N$_3$O$_2$S: C, 54.56; H, 3.13; N, 10.05. Found: C, 54.78; H, 3.46; N, 10.12.

EXAMPLE 5

8-Chloro-6-(2-chlorophenyl)-1,2-dihydro-4H-imidazo[1,5-a][1,4]benzodiazepin-1-thione-3-carboxylic acid A solution of 1.1 g (0.02 mole) of potassium hydroxide in 40 ml of methanol was treated with 2.1 g (0.005 mole) of 8-chloro-6-(2-chlorophenyl)-1,2-dihydro-4H-imidazo[1,5-a][1,4]benzodiazepin-1-thione-3-carboxylic acid methyl ester in a beaker. The solution was boiled in a steambath for 15 min and then evaporated at reduced pressure at 50°–60°. An aqueous solution of the residue was acidified with cold 6 N aqueous hydrochloric acid adding ice to keep the mixture cold. The solid was collected by filtration, washed with water and air dried on the funnel overnight to yield crude end product. Recrystallization from ethanol gave light tan crystals with mp 277°–280° (dec).

Anal. Calcd. for C$_{18}$H$_{11}$Cl$_2$N$_3$O$_2$S: C, 53.48; H, 2.74; N, 10.39. Found: C, 53.55; H, 2.92; N, 10.39.

EXAMPLE 6

8-Chloro-6-(2-chlorophenyl)-1,2-dihydro-4H-imidazo[1,5-a][1,4]benzodiazepin-1-one A mixture of 4.02 g (0.01 mole) of 8-chloro-6-(2-chlorophenyl)-1,2-dihydro-1-oxo-4H-imidazo[1,5-a][1,4]benzodiazepine-3-carboxylic acid, methyl ester, 150 ml of methanol, 15 ml of water and 2 g (0.035 mole) of potassium hydroxide was heated to reflux for 5 hours under a nitrogen atmosphere. The solution was then concentrated down to 40 ml, acidified by addition of 4 ml of glacial acetic acid and crystallized by diluting with water. The precipitate was collected, dried and recrystallized from tetrahydrofuran/methanol/ethyl acetate to yield 8-chloro-6-(2-chlorophenyl)-1,2-dihydro-1-oxo-4H-imidazo[1,5-a][1,4]benzodiazepine-3-carboxylic acid which was decarboxylated as follows: A solution of 1 g of this acid in 5 ml of ethylene glycol was heated to reflux for 45 min and then partitioned between methylene chloride and saturated sodium bicarbonate solution. The organic layer was washed with bicarbonate solution and water, dried and evaporated. Crystallization of the residue from ethyl acetate/ether gave end product which was further purified by chromatography over 20 g silica gel using methylene chloride/ethyl acetate 1:3. Crystallization from ethyl acetate/ether yielded the pure colorless product with mp 236°–238°. nmr (CDCl$_3$) δ 4.25 ppm (broad d, 1) and 4.86 (broad d, 1) (AB-system, J=13 Hz, C$_4$—H) 6.25 (d, 1, J=2 Hz, C$_3$—H) 6.98 (d, 1, J=2.5 Hz, C$_7$—H) 7.1–7.7 (m, 5, aromatic H) 8.0 (d, 1, J=8 Hz, C$_{10}$—H) 10.4 (broad s, 1, NH).

Anal. Calcd. for C$_{17}$H$_{11}$Cl$_2$N$_3$O: C, 59.32; H, 3.22; N, 12.21. Found: C, 59.41; H, 3.23; N, 12.19.

EXAMPLE 7

8-Chloro-6-(2-fluorophenyl)-1,2-dihydro-4H-imidazo[1,5-a][1,4]benzodiazepin-1-one A mixture of 0.386 g (1 mmole) of 8-chloro-1,2-dihydro-6-(2-fluorophenyl)-1-oxo-4H-imidazo[1,5-a][1,4]benzodiazepine-3-carboxylic acid, methyl ester, 10 ml of methanol, 1 ml of water and 0.225 g (4 mmole) of potassium hydroxide was heated to reflux for 3½ hours under an atmosphere of nitrogen. The solvent was evaporated and the residue was acidified with acetic acid and extracted with methylene chloride. The extracts were dried and evaporated and the residue was heated in mineral oil up to 230° for 5 min. The reaction mixture was partitioned between 1 N hydrochloric acid and methylene chloride/hexane. The acid extract was made alkaline with sodium carbonate solution and extracted with methylene chloride. The residue obtained after evaporation of the dried extracts was chromatographed over 10 g of silica gel using methylene chloride/ethyl acetate 1:2. Crystallization of the combined clean fractions from ethyl acetate/hexane yielded colorless crystals with mp 247°–250°. Uv λ max 212 mμ (ε=42250) sh 262 (10000) ir (KBr) 1695 cm$^{-1}$ (CO) 3150 (NH). Nmr (CDCl$_3$) 4.18 ppm (d, 1) and 4.88 (d, 1) (AB-system, J=12.5 Hz, C$_4$—H) 6.28 (d, 1, J=2 Hz, C$_3$—H) 6.9–7.7 (m, 5, aromatic H) 8.13 (d, 1, J=8.5 Hz, C$_{10}$—H) 10.46 (broad s, 1, NH).

Anal. Calcd. for C$_{17}$H$_{11}$ClFN$_3$O: C, 62.30; H, 3.38; N, 12.82. Found: C, 62.22; H, 3.33; N, 12.82.

EXAMPLE 8

8-Chloro-6-(2-chlorophenyl)-1,2-dihydro-2-methyl-1-oxo-4H-imidazo[1,5-a][1,4]benzodiazepine-3-carboxylic acid, methyl ester ethanolate A mixture of 1.1 g (0.02 mole) of sodium methylate and 4 g (0.01 mole) of 8-chloro-6-(2-chlorophenyl)-1,2-dihydro-1-oxo-4H-imidazo[1,5-a][1,4]benzodiazepine-3-carboxylic acid methyl ester in 100 ml of methanol was stirred under a drying tube for 30 min. The resulting pale yellow solution was treated with 5 ml of methyl iodide and stirred 5 hours longer at room temperature. After acidifying with acetic acid, the mixture was evaporated to dryness. The brown residue was partitioned between methylene chloride and water and the organic phase was separated, dried and evaporated to give a tan foam. Stirring the residue with 25 ml of ethanol gave a light tan solid. The solid was filtered, washed with a little ethanol and then with petroleum ether. Air drying on the funnel gave end product with mp ca. 120°. Recrystallization from ethanol gave off-white plates with mp 120°-125° (dec) which contained 1 mole of ethanol according to the analytical and spectral data. UV λ sh 212 mμ (ε=41000) max 281 (19800) ir (CHCl$_3$) 1700 cm$^{-1}$ (CO) 1720 (COOCH$_3$) nmr (CDCl$_3$) δ 3.60 ppm (s, 3, NCH$_3$) 3.90 (s, 3, OCH$_3$) 4.07 (d, 1) and 5.83 (d, 1) (AB-system, J=12 Hz, C$_4$—H) 7.05 (d, 1, J=2.5 Hz, C$_7$—H). 7.2-7.8 (m, 5, aromatic H) 8.03 (d, 1, J=8 Hz, C$_{10}$—H).

Anal. Calcd. for C$_{20}$H$_{15}$Cl$_2$N$_3$O$_3$C$_2$H$_5$OH: C, 57.15; H, 4.58; N, 9.09. Found: C, 57.14; H, 4.73; N, 9.16.

EXAMPLE 9

8-Chloro-6-(2-chlorophenyl)-1,2-dihydro-2-methyl-1-oxo-4H-imidazo[1,5-a][1,4]benzodiazepin-3-carboxylic acid Potassium hydroxide, 1.3 g (0.02 mole), was dissolved in 1 ml of water and added to a suspension of 4 g (0.0097 mole) of 8-chloro-6-(2-chlorophenyl)-1,2-dihydro-2-methyl-1-oxo-4H-imidazo[1,5-a][1,4]benzodiazepin-3-carboxylic acid methyl ester ethanolate in 200 ml of methanol. The solution was refluxed under argon for 3 hrs, concentrated at reduced pressure, diluted with cold water and acidified with acetic acid to give an off-white solid. The solid was washed with water and air dried on the funnel overnight to give crude end product. Recrystallization from ethanol/methylene chloride gave white crystals with mp 265°-267° (dec).

Anal. Calcd. for C$_{19}$H$_{13}$Cl$_2$N$_3$O$_3$: C, 56.74; H, 3.25; N, 10.45. Found: C, 56.50; H, 3.37; N, 10.35.

EXAMPLE 10

8-Chloro6-(2-chlorophenyl)-1,2-dihydro-2-methyl-1-oxo-4H-imidazo[1,5-a][1,4]benzodiazepin-3-carboxamide A stirred suspension of 3 g (0.0075 mole) of 8-chloro-6-(2-chlorophenyl)-1,2-dihydro-2-methyl-1-oxo-4H-imidazo[1,5-a][1,4]benzodiazepin:3-carboxylic acid in 90 ml of methylene chloride was cooled in an ice bath and treated with 1.9 g (0.009 mole) of phosphorus pentachloride in portions. Stirring in the cold under a drying tube was continued for 30 min. Ammonia was then bubbled into the cold solution for 5 min and stirring in the cold was continued 30 min. longer. Evaporation at reduced pressure gave a tan solid. The solid was stirred with 3 N ammonium hydroxide and extracted with methylene chloride. An emulsion formed but was destroyed by filtering to remove some high melting solid. The methylene chloride layer was dried over sodium sulfate and evaporated to give a yellow solid which was recrystallized from benzene to give off-white needles with mp 158°-160°. Uv λ sh 215 mμ (ε=43000) max 272 (15500) sh 330 (2500); ir (CHCl$_3$) 3510, 3400 cm$^{-1}$ (NH$_2$) 1703 (CO) 1685 (CONH$_2$).

Anal. Calcd. for C$_{19}$H$_{14}$Cl$_2$N$_4$O$_2$: C, 56.88; H, 3.52; N, 13.96. Found: C, 56.66; H, 3.70; N, 13.78.

EXAMPLE 11

8-Chloro-6-(2-chlorophenyl)-1-methylthio-4H-imidazo[1,5-a][1,4]benzodiazepin-3-carboxylic, methyl ester A stirred suspension of 10 g (0.024 mole) of 8-chloro-6-(2-chlorophenyl)-1,2-dihydro-4H-imidazo[1,5-a][1,4]benzodiazepin-1-thione-3-carboxylic acid methyl ester in 200 ml of methanol was cooled in an ice-salt bath under argon and treated with 1.25 g (0.024 mole) of sodium methylate. The argon inlet tube was replaced by a drying tube and stirring in the cold was continued for 30 min. Methyl iodide, 6 ml or 14 g (0.1 mole) was added and stirring in the cold was continued for 2 hrs. The solution was poured into cold water to give a light tan solid. The solid was filtered, washed with water and air dried on the funnel to yield crude end product. Trituration of the solid with boiling ether gave light tan prisms with mp 208°-211°. Recrystallization from ethanol gave pale yellow prisms with mp 209°-211°. Uv λ max 216 mμ (ε=50300) infl 245 (22,300) sh 270 (14,000); ir (CHCl$_3$) 1728, 1717 cm$^{-1}$ (COOCH$_3$), nmr (CDCl$_3$) δ 2.66 ppm (s, 3, SCH$_3$) 3.88 (s, 3, OCH$_3$) 3.97 (d, 1) and 5.97 (d, 1) (AB-system, J=12.5 Hz, C$_4$—H) 7-7.8 (m, 7, aromatic H).

Anal. Calcd. for C$_{20}$H$_{15}$Cl$_2$N$_3$O$_2$S: C, 55.57; H, 3.50; N, 9.72. Found: C, 55.65; H, 3.65; N, 9.77.

EXAMPLE 12

8-Chloro-6-(2-chlorophenyl)-1-methylthio-4H-imidazo[1,5-a][1,4]benzodiazepine-3-carboxamide A mixture of 3 g (0.007 mole) of 8-chloro-6-(2-chlorophenyl)-1-methylthio-4H-imidazo[1,5-a][1,4]benzodiazepine-3-carboxylic acid methyl ester and 60 ml of 25% solution of ammonia in methanol was heated at 130° in a steel bomb for 18 hrs. The contents of the bomb were evaporated at reduced pressure to give light tan crystals, which were recrystallized from methanol/methylene chloride to yield light tan prisms with mp 270°-274° (dec.). Uv λ max 217 mμ (ε=47,200) infl 242 (23,200) sh 270 (11,500), ir (KBr) 3365, 3250, 3215, 3150 cm$^{-1}$ (NH$_2$) 1675, 1650, 1590 (CON).

Anal. Calcd. for C$_{19}$H$_{14}$Cl$_2$N$_4$OS: C, 54.69; H, 3.38; N, 13.43. Found: C, 54.69; H, 3.34; N, 13.50.

EXAMPLE 13

8-Chloro-6-(2-chlorophenyl)-N-methyl-1-methylthio-4H-imidazo[1,5-a][1,4-benzodiazepine-3-carboxamide A mixture of 2.1 g (0.005 mole) of 8-chloro-6-(2-chlorophenyl)-1-methylthio-4H-imidazo[1,5-a][1,4]benzodiazepine-3-carboxylic acid methyl ester and 20 ml of a 28% solution of methylamine in ethanol was heated at 130° in a steel bomb for 18 hrs. The contents of the bomb were evaporated at reduced pressure to give a tan solid. Recrystallization from ethanol gave off-white prisms with mp 224°-227°. Uv λ max 218 mμ

($\epsilon$=51,400) infl 245 (26,000) sh 275 (12,000); ir (KBr) 3410 cm$^{-1}$ (NH) 1668, 1527 (CON).

Anal. Calcd. for $C_{20}H_{16}Cl_2N_4OS$: C, 55.69; H, 3.74; N, 12.99. Found: C, 55.63; H, 3.89; N, 12.99.

EXAMPLE 14

6-(2-Chlorophenyl)-1,8-dichloro-4H-imidazo[1,5-a][1,4]benzodiazepine-3-carboxylic acid, methyl ester A stirred mixture of 10 g (0.025 mole) of 8-chloro-6-(2-chlorophenyl)-1,2-dihydro-1-oxo-4H-imidazo[1,5-a][1,4]benzodiazepine-3carboxylic acid, methyl ester, 1 g (0.005 mole) of phosphorus pentachloride and 250 ml of phosphorus oxychloride was refluxed under a drying tube for 44 hrs. Benzene (250 ml) was added and the dark solution was evaporated in vacuo at 50°-60°. Another 250 ml of benzene was added and the solution was again evaporated to dryness at reduced pressure. The residue was dissolved in 250 ml of methylene chloride and cooled in an ice bath. Ammonia was bubbled into the cold solution for 5 min to give a tan solid. Stirring at room temperature was continued for 15 min. The mixture was filtered and evaporated at reduced pressure to give a brown gum which solidified when triturated with 75 ml of boiling ether. This solid was dissolved in about 50 ml of methylene chloride and filtered over neutral alumina. Eluted first with methylene chloride and then with 30% ethyl acetate in methylene chloride. Evaporation of the ethyl acetate methylene chloride fractions gave a tan solid which was recrystallized from ethyl acetate to give off-white prisms with mp 200°-202°. Uv $\lambda$ sh 213 m$\mu$ ($\epsilon$=44,600) infl 240 (27,500) infl 260 (20,000) infl 300 (1850) ir (CHCl$_3$) 1717 cm$^{-1}$ (COOCH$_3$).

Anal. Calcd. for $C_{19}H_{12}Cl_3N_3O_3$: C, 54.25; H, 2.88; N, 9.99. Found: C, 54.18; H, 3.10; N, 10.20.

EXAMPLE 15

6-(2-Chlorophenyl)-1,8-dichloro-4H-imidazo[1,5-a][1,4]benzodiazepine-3-carboxylic acid A solution of 2 g (0.005 mole) of 6-(2-chlorophenyl)-1,8-dichloro-4H-imidazo[1,5-a][1,4]benzodiazepine-3-carboxylic acid, methyl ester 0.7 g (0.012 mole) of potassium hydroxide, 60 ml of methanol and 2 ml of water was refluxed under argon for 2.5 hrs. The solution was evaporated in vacuo at 50°-60°. An aqueous solution of the residue was acidified with acetic acid to give a gelatinous, white precipitate. The precipitate was collected by filtration, washed with water and air dried on the funnel overnight to give off-white solid. Recrystallization from a solution of ethanol and methylene chloride gave white plates with mp 250°-253° (dec).

Anal. Calcd. for $C_{18}H_{10}Cl_3N_3O_2$: C, 53.17; H, 2.48; N, 10.33. Found: C, 53.17; H, 2.46; N, 10.21.

EXAMPLE 16

8-Chloro-6-(2-chlorophenyl)-1-methylsulfinyl-4H-imidazo[1,5-a][1,4]benzodiazepine-3-carboxylic acid, methyl ester and
8-Chloro-6-(2-chlorophenyl)-1-methylsulfonyl-4H-imidazo[1,5-a][1,4]benzodiazepine-3-carboxylic acid, methyl ester A stirred solution of 3 g (0.007 mole) of 8-chloro-6-(2-chlorophenyl)-1-methylthio-4H-imidazo[1,5-a][1,4]benzodiazepine-3-carboxylic acid, methyl ester in 60 ml of methylene chloride was cooled in an ice-salt bath and treated with 2.5 g (0.015 mole) of m-chloroperbenzoic acid in portions. Stirring in the cold was continued for 2 hrs under a drying tube. The mixture was washed with dilute ammonium hydroxide solution, dried over sodium sulfate and evaporated to give an off-white foam which solidified when triturated with boiling ether. This material was chromatographed over silica gel using 20% (v/v) of ethyl acetate in methylene chloride as eluent. The fractions containing the less polar component were combined and evaporated. Crystallization from ethanol/methylene chloride yielded the sulfone with up 220°-223°. Uv $\lambda$ max 221 m$\mu$ ($\epsilon$=41,800) infl 240 (32,000) infl 260 (18,500) infl 300 (1500); ir (KBr) 1720 cm$^{-1}$ (COOCH$_3$) 1325, 1225 (SO$_2$).

Anal. Calcd. for $C_{20}H_{15}Cl_2N_3O_4S$: C, 51.74; H, 3.26; N, 9.05. Found: C, 51.95; H, 3.41; N, 8.88.

The fractions containing the more polar major component were evaporated and the residue was crystallized from ethanol/methylene chloride to give the sulfoxide as white prisms with mp 223°-226°. Uv $\lambda$ max 220 m$\mu$ ($\epsilon$=41,000) infl 260 (12,500) infl 300 (1800); ir (KBr) 1718 cm$^{-1}$ (COOCH$_3$) 1090 (SO).

Anal. Calcd. for $C_{20}H_{15}Cl_2N_3O_3S$: C, 53.58; H, 3.37; N, 9.37. Found: C, 53.57; H, 3.52; N, 9.18.

EXAMPLE 17

8-Chloro-6-(2-chlorophenyl)-1-methoxy-4H-imidazo[1,5-a][1,4]benzodiazepine-3-carboxylic acid, methyl ester A mixture of 2.9 g (0.007 mole) of 6-(2-chlorophenyl)-1,8-dichloro-4H-imidazo[1,5-a][1,4]benzodiazepine-3-carboxylic acid methyl ester, 1.1 g (0.02 mole) of sodium methoxide and 100 ml of dry methanol was heated in a steel bomb at 115°-120° for 20 hrs. The solvent was removed at reduced pressure. The residue was dissolved in methylene chloride, washed with dilute hydrochloric acid to give pale yellow amorphous solid. An ethereal solution (60 ml) of the solid was washed with dilute ammonium hydroxide solution, dried, filtered and concentrated on a steam bath to about 20 ml. White crystals were obtained after keeping the solution at room temperature for several hours with occasional scratching. Recrystallization from ether gave white crystals with mp 155°-160°. Uv $\lambda$ sh 213 m$\mu$ ($\epsilon$=36,000) max 266 (20,500) ir (CHCl$_3$) 1715 cm$^{-1}$ (COOCH$_3$); nmr (CDCl$_3$) $\delta$ 3.93 ppm (s, 3, COOCH$_3$) 4.23 (s, 3, OCH$_3$) 4.08 (d, 1) and 6.06 (d, 1) AB-system, J=12 Hz, C$_4$—H) 7.1-7.9 (m, 7, aromatic H).

Anal. Calcd. for $C_{20}H_{15}Cl_2N_3O_3$: C, 57.71; H, 3.63; N, 10.09. Found: C, 57.72; H, 3.57; N, 10.02.

EXAMPLE 18

8-Chloro-6-(2-chlorophenyl)-1-methoxy-4H-imidazo[1,5-a][1,4]benzodiazepine-3-carboxamide A mixture of 0.3 g (0.00074 mole) of 6-(2-chlorophenyl)-1,8-dichloro-4H-imidazo[1,5-a][1,4]benzodiazepine-3-carboxamide, 1.15 g (0.0028 mole) of sodium methoxide and 15 ml of methanol was heated at 120°-125° in a steel bomb for 24 hrs. The solvent was evaporated in vacuo. The residue was dissolved in methylene chloride, washed with water, dried and evaporated at reduced pressure to give a tan, amorphous solid. After chromatography over silica gel using 5% (v/v) of ethanol in methylene chloride the solid was recrystallized from a solution of ethanol and methylene chloride to give off-white crystals with mp 235°-238° (dec). Uv $\lambda$ max 216 m$\mu$ ($\epsilon$=41,000) sh 243 (22,600) max 264 (20,000); ir (KBr) 3445, 3330, 3280 cm$^{-1}$ (NH$_2$) 1675 (CON) nmr (d-DMSO) $\delta$ 4.0 ppm (d, 1) and 5.88

(d, 1) (AB-system, J=12 Hz, C$_4$—H) 4.06 (s, 3, OCH$_3$) 6.9-7.9 (m, 9, aromatic H and NH$_2$).

Anal. Calcd. for C$_{19}$H$_{14}$Cl$_2$N$_4$O$_2$: C, 56.87; H, 3.52; N, 13.96. Found: C, 56.85; H, 3.41; N, 13.71.

EXAMPLE 19

6-(2-Chlorophenyl)-1,8-dichloro-4H-imidazo[1,5-a][1,4]benzodiazepine-3-carboxamide A mixture of 0.5 g (0.0012 mole) of 6-(2-chlorophenyl)-1,8-dichloro-4H-imidazo[1,5-a][1,4]benzodiazepine-3-carboxylic acid methyl ester and 20 ml of a 20% solution of ammonia in methanol was heated at 120°-125° in a steel bomb for 18 hrs. Evaporation of the solvent at reduced pressure gave an amorphous solid. The solid was dissolved in methylene chloride, washed with water, dried and evaporated at reduced pressure to give a tan, amorphous solid which crystallized when stirred with a small amount of boiling ether. Recrystallization from a solution of methanol and methylene chloride gave white crystals with mp 285°-288°. Uv λ 214 mμ ($\epsilon$=44,300) sh 245 (26,500) sh 260 (16,400) sh 300 (600); ir (KBr) 3470, 3335 cm$^{-1}$ (NH$_2$) 1670 (CON).

Anal. Calcd. for C$_{18}$H$_{11}$Cl$_3$N$_4$O: C, 53.29; H, 2.73; N, 13.81. Found: C, 53.34; H, 2.77; N, 13.75.

EXAMPLE 20

6-(2-Chlorophenyl)-1,8-dichloro-N-methyl-4H-imidazo[1,5-a][1,4]benzodiazepine-3-carboxamide and 8-chloro-6-(2-chlorophenyl)-1-methylamino-N-methyl-4H-imidazo[1,5-a][1,4]benzodiazepine-3-carboxamide A mixture of 2.4 g (0.0056 mole) of 6-(2-chlorophenyl)-1,8-dichloro-4H-imidazo[1,5-a][1,4]benzodiazepine-3-carboxylic acid methyl ester and 80 ml of a 21% solution of methylamine in ethanol was heated in a steel bomb at 120°-130° for 64 hrs. Evaporation of the solution at reduced pressure gave a gum which was dissolved in methylene chloride. The solution was washed with water, dried and evaporated. The residue was chromatographed over 70 g of silica gel using 5% (v/v) of tetrahydrofuran in ethyl acetate as eluant. The fractions containing the less polar component were combined and evaporated. Crystallization from methylene chloride/ethyl acetate gave the dichloro product which was recrystallized from ethanol/methylene chloride for analysis to give white prisms with mp 225°-228°. Uv λ max 216 mμ ($\epsilon$=43,800) sh 240 (28,600) sh 260 (17,00) sh 303 (1050) ir (CHCl$_3$) 3435 cm$^{-1}$ (NH) 1675 (CON); nmr (CDCl$_3$) δ 2.97 (d, 3, J=5 Hz, NHC$\underline{H}_3$) 4.0 (d, 1) and 6.26 (d, 1) (AB-system, J=12.5 Hz, C$_4$—H) 6.8-7.9 (m, 8, aromatic H and NH).

Anal. Calcd. for C$_{19}$H$_{13}$Cl$_3$N$_4$O: C, 54.38; H, 3.12; N, 13.35. Found: C, 54.39; H, 3.07; N, 13.43.

Evaporation and crystallization of the later fractions containing the more polar component yielded the monochloro product. Recrystallization from ether/methanol gave off-white crystals with mp 208°-210°. Uv λ sh 215 mμ ($\epsilon$=42,600) sh 245 (17,300) max 274 (10,400) sh 293 (7600); ir (CHCl$_3$) 3425 cm$^{-1}$ (NH) 1655 (CON); nmr (CDCl$_3$) δ 2.90 (d, 3, J=5 Hz, NHCH$_3$) 2.97 (d, 3, J=5 Hz, NHCH$_3$) 3.97 (d, 1) and 6.13 (d, 1) (AB-system, J=12.5 Hz, C$_4$—H) 4.08 (q, 1, J=5 Hz, —N$\underline{H}$CH$_3$) 6.8-7.8 (m, 8, aromatic H and CONH).

Anal. Calcd. for C$_{20}$H$_{17}$Cl$_2$N$_5$O: C, 57.98; H, 4.14; N, 16.90. Found: C, 57.99; H, 4.26; N, 16.90.

EXAMPLE 21

Compounds of Example 3 may be alternately prepared by reaction of 7-chloro-5-(2-fluorophenyl)-2-[(amino)methoxycarbonylmethylene]-1,3-dihydro-2H-1,4-benzodiazepine with phosgene as described in Example 2.

EXAMPLE 22

8-Chloro-6-(2-fluorophenyl)-2,3,3a,4-tetrahydro-1H-imidazo[1,5-a] [1,4]benzodiazepin-1-one A solution of 5 g (0.0165 mole) of 2-aminomethyl-7-chloro-2,3-dihydro-5-(2-fluorophenyl)-1H-1,4-benzodiazepine in 100 ml of methylene chloride was stirred and cooled in a dry ice-acetone bath. To this solution, 22.7 ml (0.02 mole) of a 10-12% solution of phosgene in benzene was added, followed by 2 ml of pyridine. The mixture was stirred for 10 minutes on the cooling bath and then for 10 minutes after removal of the bath. A saturated solution of sodium bicarbonate, 250 ml., was added and stirring was continued for another 10 minutes. The methylene chloride layer was separated, dried and evaporated to yield an oil. This oil was chromatographed over 100 g of silica gel (Merck, 70-230 mesh) using 10% (v/v) of ethanol in methylene chloride. Fractions containing product were combined and evaporated to give oil, which upon crystallization from ether yielded crystals with mp 178°-180°. Recrystallization for analysis from methylene chloride/ethyl acetate gave colorless crystals with mp 181°-183°.

Anal. Calcd. for C$_{17}$H$_{13}$ClFN$_3$O: C, 61.92; H, 3.97; N, 12.74. Found: C, 61.87; H, 4.01; N, 12.65.

Uv (2-PrOH) λ infl 240 mμ ($\epsilon$=19000) infl 270 (4700) infl 315 (1000) IR (CHCl$_3$) 3450, 3250 cm$^{-1}$ (NH) 1710 (CO) NMR(CDCl$_3$) δ 3.4-4.2 ppm (m, 4, C$_3$—H, C$_4$—H), 4.6 (m, 1, C$_{3a}$—H) 5.55 (broad s, 1, NH) 6.8-7.7 (m, 7, aromatic H).

EXAMPLE 23

8-Chloro-6-(2-fluorophenyl)-2,3,3a,4-tetrahydro-1H-imidazo[1,5-a][1,4]benzodiazepine-1-thione To a solution of 15.0 g. (49.5 mmol) of 2-aminomethyl-7-chloro-2,3-dihydro-5-(2-fluorophenyl)-1H-1,4-benzodiazepine in 200 ml. of methylene chloride, cooled in a dry ice-acetone bath, was added a solution of 9.2 g (80 mmol) of thiophosgene in 15 ml. of methylene chloride followed by 16.0 g (160 mmol) of triethylamine. After 10 minutes the bath was removed and the mixture allowed to warm to room temperature with stirring. After an additional 5 min, 200 ml of saturated aqueous sodium bicarbonate was added, stirred 15 min, and filtered to give the crude product. The organic layer from the filtrate was removed, dried with anhydrous sodium sulfate and evaporated in vacuo to give additional product. An analytical sample was obtained by recrystallization from methylene chloride-petroleum ether, mp 233°-237°; Ir (KBr) 1580 and 1460 cm$^{-1}$; nmr (DMSO-d$_6$) 3.40-4.30 δ (m, 4H), 4.60-5.30 (m, 1H) and 7.00-8.50 (m, 8H); uv λ max 227 nm ($\epsilon$=25830), infl. 277 (4400), infl. 318 (1064).

Anal. Calcd. for C$_{17}$H$_{13}$ClFN$_3$S: C, 59.05; H, 3.79; N, 12.15. Found: C, 58.97; H, 3.69; N, 12.02.

EXAMPLE 24

8-Chloro-3a,4-dihydro-6-(2-fluorophenyl)-1-methylthio-3H-imidazo[1,5-a][1,4]benzodiazepine A solution of 8.3 g (24 mmol) of end product of Example 23 and 4.8 ml of dimethyl sulfate in 300 ml of ethanol was heated on a steam bath for 30 min, cooled, evaporated in vacuo and treated with 50 ml 2N sodium hydroxide and warmed for a few minutes. The mixture was diluted with water, extracted with methylene chloride, dried with anhydrous sodium sulfate, evaporated in vacuo and the residue treated with ether to give the crude product. Recrystallization from methylene chloride ether gave a white powder, mp 163°–165°: Ir (KBr) 1580 and 1480 cm$^{-1}$; nmr (CDCl$_3$) 2.40 (s, 3H), 3.40–4.30 (m, 4H), 4.60–5.00 (m, 1H) and 6.80–7.60 (m, aromatic, 7H); uv λ max infl. 240 nm ($\epsilon$=11800) and infl. 280 (3400); mass spectrum m/e 359 (M+).

Anal. Calcd. for C$_{18}$H$_{15}$ClFN$_3$S: C, 60.08; H, 4.70; N, 11.68. Found: C, 60.22; H, 4.17; N, 11.85.

EXAMPLE 25

8-Chloro-6-(2-fluorophenyl)-1-methylthio-4H-imidazo[1,5-a][1,4]benzodiazepine

A mixture of 2.8 g (7.8 mmol) of the end product of Example 24 and 13 g of activated manganese dioxide in 500 ml of toluene was refluxed overnight. The mixture was filtered through Celite, evaporated in vacuo and the residue treated with ether-petroleum ether to give a tan solid. Recrystallization from methylene chloride-ether gave a white powder, mp 180°–181°: Ir (KBr) 1610 and 1480 cm$^{-1}$; nmr (CDCl$_3$) 2.60 δ (s, 3H), 4.10 (d, J=12Hz, 1H) 5.20 (d, J=12Hz, 1H) and 6.90–7.80 (m, aromatic, 8H); uv λ max 219 nm ($\epsilon$=36500), infl. 242 (19900) and 270 (8700); mass spectrum m/e 357 (M+).

Anal. Calcd. for C$_{18}$H$_{13}$ClFN$_3$S: C, 60.42; H, 3.66; N, 11.74. Found: C, 60.32; H, 3.43; N, 12.00.

EXAMPLE 26

8-Chloro-6-(2-fluorophenyl)-1-methylsulfinyl-4H-imidazo[1,5-a][1,4]benzodiazepine A solution of 450 mg (1.25 mmol) of the end product of Example 25 in 10 ml of acetic acid and 1 ml of 30% hydrogen peroxide was allowed to stand at room temperature overnight. The solution was treated with ice and ammonium hydroxide; the resulting solid was collected, washed with water, dissolved in methylene chloride, treated with anhydrous sodium sulfate and charcoal, filtered and evaporated in vacuo to a white foam, mp 95°–110°: Ir (KBr) 1610, 1480 and 1047 cm$^{-1}$; nmr (CDCl$_3$) 2.95 (s, 3H), 4.15 (d, J=13Hz, 1H), 5.25 (d, J=13Hz, 1H), 6.95–8.40 (m, aromatic, 8H); uv λ max 219 nm ($\epsilon$=37500), infl. 243 (20000); sh. 265 (13700), infl. 305 (1200); mass spectrum m/e 373 (M+).

Anal. Calcd. for C$_{18}$H$_{13}$ClFN$_3$OS: C, 57.83; H, 3.50; N, 11.24. Found: C, 57.61; H, 3.54; N, 11.17.

EXAMPLE 27

8-Chloro-6-(2-fluorophenyl)-1-methylsulfonyl-4H-imidazo[1,5-a][1,4]benzodiazepine-5-oxide A solution of 2.0 g (5.57 mmol) of the end product of Example 25 in 40 ml of acetic acid and 9 ml of 30% hydrogen peroxide was heated on a steam bath for 45 min. The solution was diluted with water and neutralized with ammonium hydroxide. The resulting solid was washed with water, triturated with methanol and washed with ether to give a white foam which was recrystallized from methylene chloride-petroleum ether and then methylene chloride-methanol to give white prisms, mp 219°–220°: Ir (KBr) 1326 and 1137 cm$^{-1}$; nmr (DMSO-d$_6$) 3.30 δ (s, 3H), 5.10 (s, broad, 2H), 6.90–7.90 (m, aromatic, 8H); uv λ max 217 nm ($\epsilon$=25500), infl. 235 (22850), sh. 270 (14800), 300 (10200); mass spectrum m/e 405 (M+).

Anal. Calcd. for C$_{18}$H$_{13}$ClFN$_3$O$_3$S: C, 53.27; H, 3.23. Found: C, 53.46; H, 3.30.

EXAMPLE 28

| Capsule Formulation | mg/capsule | | | |
|---|---|---|---|---|
| 8-Chloro-6-(2-chlorophenyl)-1-thiomethyl-4H-imidazo[1,5-a][1,4]benzodiazepin-3-carboxamide | 1.0 | 5.0 | 10.0 | 40.0 |
| Lactose | 149.0 | 182.5 | 215.0 | 260.0 |
| Cornstarch | 40.0 | 50.0 | 60.0 | 80.0 |
| Magnesium Stearate | 2.0 | 2.5 | 3.0 | 4.0 |
| Talc | 8.0 | 10.0 | 12.0 | 16.0 |
| Total | 200 mg | 250 mg | 300 mg | 400 mg |

Procedure (1) Mix Items 1–3 in a suitable mixer. Mill through suitable mill.

(2) Mix with Items 4 and 5 and fill on capsule machine.

EXAMPLE 29

| Capsule Formulation | mg/capsule | | | |
|---|---|---|---|---|
| 8-Chloro-6-(2-chlorophenyl)-1-thiomethyl-4H-imidazo[1,5-a][1,4]benzodiazepin-3-carboxamide | 1.0 | 5.0 | 10.0 | 40.0 |
| Lactose, Anhydrous DTG | 127.0 | 142.5 | 182.0 | 216.0 |
| Microcrystalline Cellulose | 40.0 | 50.0 | 60.0 | 80.0 |
| Modified Starch | 10.0 | 12.5 | 15.0 | 20.0 |
| Cornstarch | 20.0 | 25.0 | 30.0 | 40.0 |
| Magnesium Stearate | 2.0 | 2.5 | 3.0 | 4.0 |
| Total | 200 mg | 250 mg | 300 mg | 400 mg |

Procedure (1) Mix Items 1–5 in a suitable mixer for 1 to 15 minutes.

(2) Add Item 6 and mix for 5 minutes. Compress on a suitable press.

EXAMPLE 30

| Capsule Formulation | mg/capsule | | | |
|---|---|---|---|---|
| 8-Chloro-6-(2-chlorophenyl)-1-thiomethyl-4H-imidazol[1,5-a][1,4]benzodiazepin-3-carboxamide | 1.0 | 5.0 | 10.0 | 40.0 |
| Lactose | 195.0 | 230.0 | 264.0 | 273.0 |
| Pregelatinized Starch | 12.5 | 15.0 | 17.5 | 20.0 |
| Cornstarch | 25.0 | 30.0 | 35.0 | 40.0 |
| Modified Starch | 12.5 | 15.0 | 17.5 | 20.0 |
| Magnesium Stearate | 4.0 | 5.0 | 6.0 | 7.0 |
| Total | 250 mg | 300 mg | 350 mg | 400 mg |

Procedure (1) Mix Items 1–5 in a suitable mixer, granulate with water. Dry overnight in an oven. Mill through a Fitzpatrick mill.

(2) Mix with Item 6 and compress on a suitable press.

EXAMPLE 31

The compound 8-Chloro-6-(2-chlorophenyl)-1-methoxy-4H-imidazo[1,5-a][1,4]benzodiazepine-3-carboxylic acid methyl ester can be formulated by following the Examples of 28–30.

EXAMPLE 32
The compound 8-Chloro-6-(2-chlorophenyl)-1,2-dihydro-1-oxo-4H-imidazo[1,5-a][1,4]benzodiazepine-3-carboxylic acid, methyl ester, ethanolate can be formulated by following the Examples of 28–30.
We claim:
1. A compound of the formula
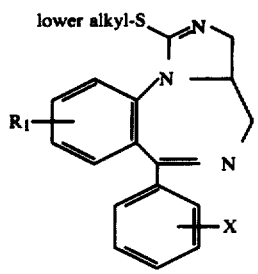
wherein $R_1$ is hydrogen, halogen or trifluoromethyl; and X is hydrogen or halogen.
* * * * *